(12) United States Patent
Een et al.

(10) Patent No.: US 11,033,439 B2
(45) Date of Patent: Jun. 15, 2021

(54) ELASTIC LAMINATE AND PROCESS FOR THE MANUFACTURE OF ELASTIC LAMINATE

(71) Applicant: SCA Hygiene Products AB, Gothenburg (SE)

(72) Inventors: Hans Een, Mölnlycke (SE); Lucas Bäck, Billdal (SE); Inge Wågdahl, Kållered (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 336 days.

(21) Appl. No.: 14/653,871

(22) PCT Filed: Dec. 21, 2012

(86) PCT No.: PCT/SE2012/051475
§ 371 (c)(1),
(2) Date: Jun. 19, 2015

(87) PCT Pub. No.: WO2014/098683
PCT Pub. Date: Jun. 26, 2014

(65) Prior Publication Data
US 2015/0328056 A1    Nov. 19, 2015

(51) Int. Cl.
*A61F 13/49*    (2006.01)
*A61F 13/15*    (2006.01)

(52) U.S. Cl.
CPC .... *A61F 13/4902* (2013.01); *A61F 13/15577* (2013.01); *A61F 13/15699* (2013.01);
(Continued)

(58) Field of Classification Search
None
See application file for complete search history.

(56) References Cited

U.S. PATENT DOCUMENTS

| 4,666,542 A | 5/1987 | De Jonckheere | |
| 4,720,415 A * | 1/1988 | Vander Wielen | B32B 5/04 428/152 |

(Continued)

FOREIGN PATENT DOCUMENTS

| CN | 1969002 A | 5/2007 |
| EP | 1666178 | 6/2006 |

(Continued)

OTHER PUBLICATIONS

Canadian Office Action dated Jun. 7, 2016 issued in corresponding Canadian patent application No. 2,895,643 (5 pages).

(Continued)

*Primary Examiner* — Shawn Mckinnon
(74) *Attorney, Agent, or Firm* — Buchanan Ingersoll & Rooney PC

(57) ABSTRACT

An elastic laminate including a first nonwoven layer, a second nonwoven layer, and a plurality of elastic strands arranged in parallel with one another between said first and second nonwoven layers is disclosed, as well as a process for the production of the laminate. The elastic laminate includes elastic strands that are stretched and individually coated with an adhesive. The first and second nonwoven layers are attached to the stretched elastic strands to provide a corrugated elastic laminate when the elastic strands are relaxed. At least one of the nonwoven layers is attached to the strands at distinct adhesive bonding points in a repeating predetermined pattern in a lengthwise direction along the strands to form a predetermined corrugation pattern, and the nonwoven layers are substantially free of adhesive, except in the adhesive bonding points where the layers are attached to the elastic strands.

18 Claims, 15 Drawing Sheets

(52) U.S. Cl.
CPC .. *A61F 13/15707* (2013.01); *A61F 13/49011* (2013.01); *A61F 2013/49025* (2013.01); *A61F 2013/49031* (2013.01); *Y10T 442/602* (2015.04)

(56) References Cited

U.S. PATENT DOCUMENTS

| | | | |
|---|---|---|---|
| 5,209,801 | A | 5/1993 | Smith |
| 5,681,302 | A | 10/1997 | Melbye et al. |
| 5,964,973 | A | 10/1999 | Heath et al. |
| 6,387,471 | B1 | 5/2002 | Taylor et al. |
| 6,902,796 | B2 * | 6/2005 | Morell .............. A61F 13/15593 428/292.1 |
| 2001/0030014 | A1 | 10/2001 | Kwok |
| 2003/0089447 | A1 | 5/2003 | Molee et al. |
| 2004/0158217 | A1 | 8/2004 | Wu et al. |
| 2004/0219854 | A1 | 11/2004 | Groitzsch et al. |
| 2005/0013975 | A1 | 1/2005 | Brock et al. |
| 2006/0142728 | A1 | 6/2006 | Tabor et al. |
| 2006/0270302 | A1 | 11/2006 | Ando et al. |
| 2007/0135008 | A1 * | 6/2007 | Hall ........................ C08L 23/02 442/181 |
| 2008/0306194 | A1 | 12/2008 | Sun et al. |
| 2012/0258246 | A1 | 10/2012 | Saine et al. |

FOREIGN PATENT DOCUMENTS

| | | |
|---|---|---|
| JP | H10-501195 | 2/1998 |
| JP | 2002-291796 | 10/2002 |
| JP | 2003-136591 | 5/2003 |
| JP | 2005-212405 | 8/2005 |
| JP | 2006-27089 A | 2/2006 |
| JP | 2011-505946 | 3/2011 |
| WO | WO-2008/064287 A1 | 5/2008 |
| WO | WO 2009/074922 | 6/2009 |

OTHER PUBLICATIONS

Official Letter dated Mar. 1, 2017, accompanied by a Search Report issued in corresponding Taiwanese patent application No. 102142055 (6 pages) and its partial English-language translation thereof (5 pages).

English-language translation on a First Chinese Office Action dated Feb. 28, 2017 issued in corresponding Chinese patent application No. 201280077762.0 (10 pages).

English Language translation of a Japanese Office Action dated Jun. 5, 2017 issued in corresponding Japanese patent application No. 2015-549305 (6 pages).

English-language translation of a Japanese Office Action dated Sep. 16, 2016 issued in corresponding Japanese patent application No. 2015-549305 (4 pages).

Colombian Office Action No. 28580 dated May 23, 2017 issued in corresponding Colombian patent application No. 15165991 (17 pages) and its partial English-language translation of relevant parts thereof (12 pages).

Colombian Patent Office, Office Action for Colombian Patent Application No. 15165991, dated Feb. 25, 2019 (partial translation attached).

English-language translation of a Written Opinion and Search Report dated Oct. 7, 2019 issued in Brazilian patent application No. BR112015015014-4.

* cited by examiner

ELASTIC LAMINATE AND PROCESS FOR THE MANUFACTURE OF ELASTIC LAMINATE

CROSS-REFERENCE TO PRIOR APPLICATION

This application is a § 371 National Stage Application of PCT International Application No. PCT/SE2012/051475 filed Dec. 21, 2012, which is incorporated herein in its entirety.

TECHNICAL FIELD

The present disclosure relates to an elastic laminate including a first nonwoven layer, a second nonwoven layer and a plurality of elastic strands in between the nonwoven layers. The disclosure relates to a process for the production of the elastic laminate, and the use of the elastic laminate in absorbent products.

BACKGROUND

Absorbent products of disposable type, such as diapers, training pants and incontinence products are well known. Typically, such products include a liquid-permeable top sheet, a liquid-impermeable backsheet and an absorbent core, which is adapted to absorb liquids, such as urine and/or blood. These products often include elastic web elements to improve fit of the product to the body of the wearer, and the elastic elements may be incorporated for example on the waist region, stomach region or leg regions.

It is known to produce elasticized webs or laminates in a number of different ways. Traditionally, one or more elastic strands are elongated by a tensioning force and is affixed using adhesive to a non-tensioned substrate, which is then gathered when the strands are relaxed. The adhesive may be applied by means of spraying to the elongated elastic strands and to the non-tensioned substrate before the elongated strands are made to contact the substrate to form the elastic web or laminate. After the elongated strand and the non-tensioned substrate have been brought in contact, the tensioning force on the strands is removed, and the strands are relaxed. The elastic strands then contract back towards their original, non-tensioned length, thereby gathering the substrate and thus forming a corrugated web or laminate. Such production method has been disclosed for example by U.S. Pat. No. 5,964,973.

However, there are some drawbacks with the above-described production technology and the product obtained. For example, there is a risk that the adhesive is applied in an irregular manner on the product, whereby an uneven surface structure is obtained for the laminate. Also, the components of the production machinery, as well as undesired areas of the product may become contaminated by the adhesive. The adhesive tends to stiffen the product in those areas where an adhesive is present. These areas become less flexible than those areas having no adhesive. Also, if the adhesive is applied evenly over the surface of the nonwoven material, the adhesive will stiffen the nonwoven material and may make it less flexible. The stiffness and inflexibility also affects the product in such a way that when the product is folded, permanent folding marks arise in the product. In addition, the adhesive tends to reduce the breathability of the product, something which may be disadvantageous in products such as disposable diapers, where air permeability is often desired.

However, adhesives are nevertheless desirable in the production of elastic laminates, since they are well-known in the art, safe, stable in the production and present an economic alternative for manufacturing laminates.

SUMMARY

It is desired to provide an elastic laminate having improved smoothness, softness, flexibility and breathability, as compared with laminates obtained as described above. It is also desired to reduce problems associated with the traditional adhesive spray technology in the production of elastic laminates and the problems experienced with the products produced by the process.

These problems are solved or at least substantially reduced by an elastic laminate that includes a first nonwoven layer and a second nonwoven layer and a plurality of elastic strands arranged in parallel with one another between the first and second nonwoven layers. The elastic strands are stretched and individually coated with an adhesive, and the nonwoven layers are attached to the stretched elastic strands to provide a corrugated elastic laminate when the elastic strands are relaxed. At least one of the nonwoven layers is attached to the strands at distinct adhesive bonding points in a repeating predetermined pattern in a lengthwise direction along the strands to form a predetermined corrugation pattern. The nonwoven layers are substantially free of adhesive, except where the layers are attached to the elastic strands. Thereby, the obtained laminate is soft, flexible and breathable. The predetermined pattern gives the laminate surface a smooth feeling.

In particular embodiments, the laminate is elastic in the longitudinal direction of the strands and the predetermined corrugation pattern crosses the direction of the elastic strands at an angle α of at least 45°, at least 60°, at least 80°, or at least 85° to the direction of the elastic strands. The angle could be in a corresponding way over 90°, but less than 95°. Alternatively, the angle α can be equal to or less than 135°. In case of wave- or zigzag-shaped lines, it is the central axis of the wave shaped and zigzag shaped lines that is angled to the direction of the elastic strands. The corrugation pattern can also cross the direction of the elastic strands at an angle of 90°. In other embodiments, the pattern is slightly inclined in relation to the longitudinal direction of the strands to decrease line pressure variations in a compression device in which the corrugation pattern is formed. Also, line pressure can be retained more stable over the whole width of the elastic strands during the production if the corrugation pattern is slightly inclined, whereby for example vibrations can be decreased. If the corrugation pattern is at an exact angle of 90° in relation to the longitudinal direction of the strands, there may be a risk for an increased line pressure which may cause bouncing and thereby vibrations in the compression device.

The lines of the corrugation pattern can be parallel to each other. In this way, it is possible to form a corrugation pattern by means of a compression device which is arranged to extend over the entire width of the laminate web, and it can be assured that the distinct adhesive bonding points are present on each elastic strand.

The predetermined corrugation pattern may include straight lines or wave-shaped lines or lines with a zig zag shape in the extension direction of the lines. The shape of the corrugation pattern provides a visual effect on the laminate while it is assured that sufficient amount of adhesive bonding points are provided along the elastic strands.

A lot of different nonwoven materials may be used. The first and/or the second nonwoven layer may include meltblown and/or spunbond and/or spunlaced spunbond nonwoven layer. Since the nonwoven materials may have different kinds of surface properties, it is possible to affect the surface characteristics of the laminate by using different kind of materials.

The present disclosure relates also to a process for the manufacture of an elastic laminate in a lamination process. The process includes the steps of feeding a first nonwoven web to the lamination process and feeding a second nonwoven web to the lamination process. The first and second nonwoven webs form the first and second nonwoven layers or the laminate, respectively. Also, a plurality of elastic strands arranged in parallel are fed to the lamination process. The elastic strands are stretched before being coated individually with an adhesive. After the adhesive coating, the first and second nonwoven webs and the stretched adhesive coated elastic strands are brought together and compressed by means of a compression device including a first compression means and a second compression means to form a laminate. The at least first compression means has a predetermined surface pattern to form distinct adhesive bonding points in a repeating predetermined pattern in a lengthwise direction along the elastic strands. After compression the elastic strands are relaxed in the formed laminate to form a corrugated elastic laminate with a predetermined corrugation pattern. By the process, a soft, smooth, flexible and breathable elastic laminate can be produced.

In particular embodiments, the elastic strands are coated by means of slot-coating. By slot coating is meant that an adhesive is applied to elastic strands in a slot or cavity which is provided with an adhesive. The slot coating device may be for example V-slot or a comb-slot device. By slot coating it can be assured that each strand obtains a sufficient amount of adhesive coating while areas outside the elastic strands can be kept free of adhesive. Also, process equipment can be protected from contamination.

The first compression means may have a protruding straight-line shaped surface structure. Therefore, it can be assured that there is equal number of adhesive bonding points on each elastic strand, and that the bonding points are evenly distributed.

The first compression means may also have a protruding wave-shaped line surface structure. This provides an effective visual effect on the corrugation pattern, while it ensures that a sufficient number of adhesive bonding points is evenly provided on each elastic strand.

The first compression means can be a compression cylinder. By using a cylinder in the process, it is possible to provide continuous compression of the nonwoven layers and the strands.

The present disclosure also relates to an absorbent product including the elastic laminate described above. The elastic laminate can be included in the waist and/or hip region of the absorbent product.

BRIEF DESCRIPTION OF THE DRAWINGS

Embodiments of the invention will be described in the following by way of example only and with reference to the attached drawings, in which Figures (Fig.).

DETAILED DESCRIPTION OF PARTICULAR EMBODIMENTS

Figure 1:
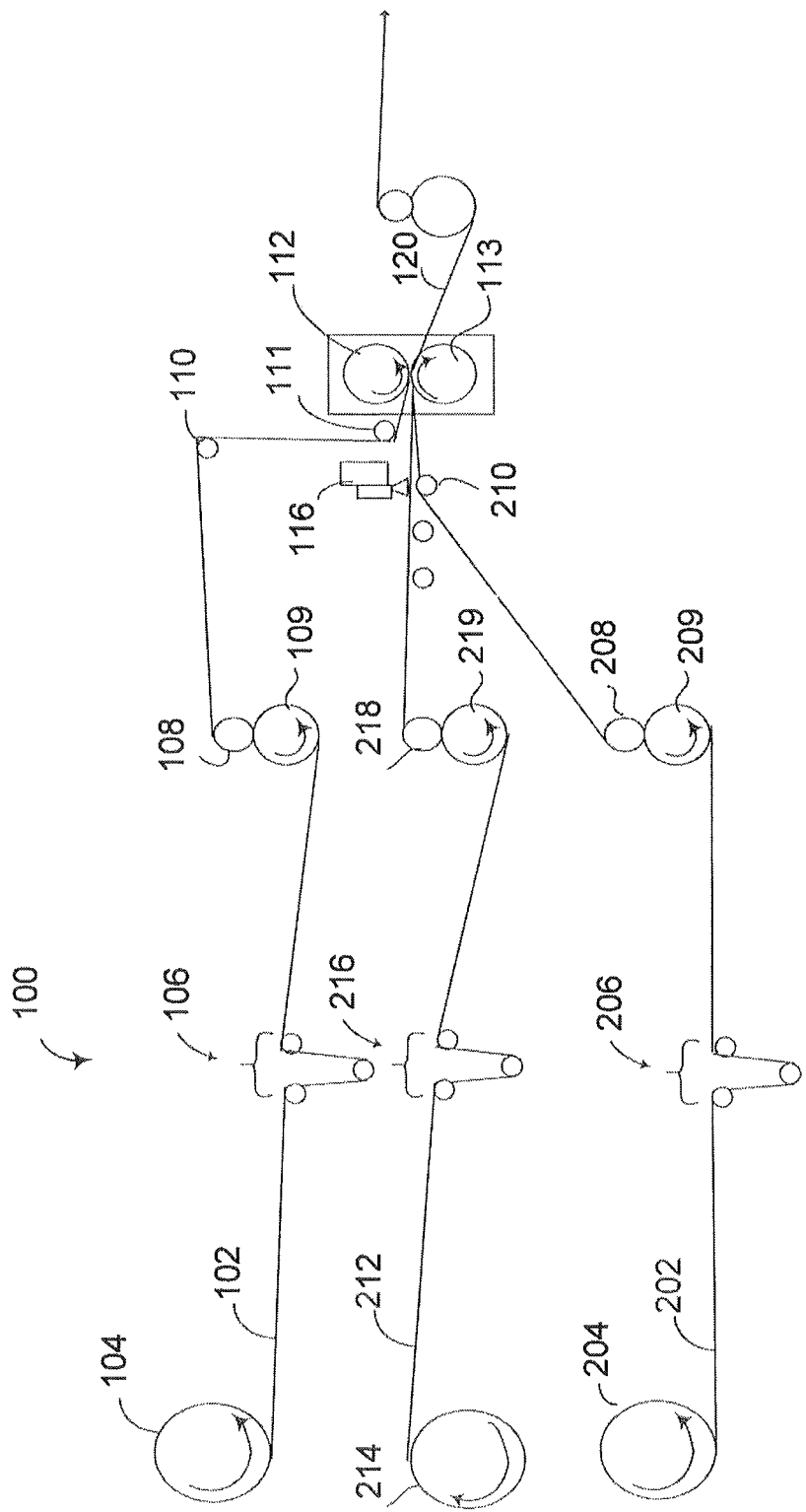
FIG. 1 is a schematic view of a prior art process to produce an elastic laminate.

FIG. 1 shows schematically a prior art lamination process 100 for the production of a prior art elastic laminate including a first and a second nonwoven web and a plurality of elastic strands in between the nonwoven webs. The first nonwoven web 102 is fed from a nonwoven web roll 104 through dancer cylinders 106 to nip cylinders 108, 109, and then through guide cylinders 110, 111 to compression cylinders 112, 113.

In a similar way, a second nonwoven web 202 is fed from a nonwoven web roll 204 through dancer cylinders 206 to nip cylinders 208, 209, and then through a guide cylinder 210 to the compression cylinders 112, 113.

The dancer cylinders 106; 206 adjust the tension of the nonwoven webs. The plurality of elastic strands 212 are fed to the process in parallel from a multi-strand roller 214. The strands are tensioned by means of dancer rollers 216 to an extension of at least 30%. The strands are then fed to the nip rollers 218, 219, in which all the webs and strands are in phase. The strands are then coated with an adhesive by means of a spray application device 116.

After the spray application, the webs 102, 202 and elastic strands 212 are gathered between compression rollers 112, 113 to form an elastic laminate 120. In this prior art process, the compression cylinders 112, 113 have substantially flat surfaces, i.e. the cylinders do not have any special surface structure. The formed elastic laminate will obtain a random surface structure.

As can be seen from FIG. 1, the second web is guided to pass under the elastic strands 212 in a position where adhesive is sprayed onto the web by means of the spray application device 116. Therefore, also the second nonwoven web will be at least partly coated with the adhesive. When the two nonwoven webs and the elastic strands are combined part of the adhesive will be transferred to the first nonwoven.

Figure 2:
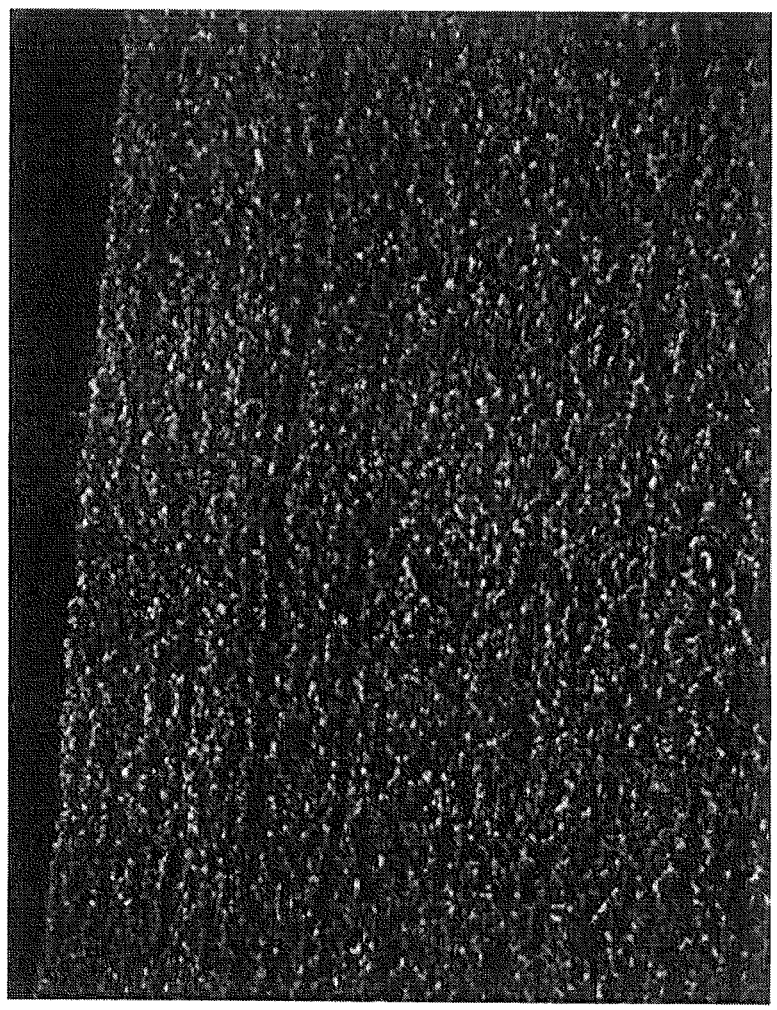
FIG. 2 is a photographic representation of a prior art spray pattern.

FIG. 2 shows a photograph of the prior art spray coated elastic strands. As can be seen, the adhesive is applied on the surface in an irregular and random manner. Part of the adhesive will also be transferred to the nonwoven between the strands. The product suffers from the drawbacks listed above, e.g. the strands are unevenly coated, whereby an uneven surface structure is obtained for the laminate. The adhesive on the nonwoven will make the nonwoven materials stiffer. Also when the strands are evenly coated with the adhesive and are fastened to the nonwoven materials along the whole length of the strands, the result will be an uneven surface structure for the laminate.

The laminate includes nonwoven layers attached to elastic strands at distinct adhesive bonding points in a predetermined pattern, the nonwoven layers are substantially free of adhesive, except where the layers are attached to the elastic strands. By substantially free of adhesive is meant that no adhesive is added to the areas outside the elastic strands, but small amounts of adhesive may be transferred from the elastic strands to the nonwoven layers outside the adhesive bonding points.

The process described herein differs from the prior art mainly in the manner of applying adhesive in the laminate, and in the manner of compressing the nonwoven webs.

In the present process each individual strand is coated separately, such as by means of a slot coating device which can be for example a V-slot or comb-slot-coating device. By the comb-slot or comb-coater is meant in this case a slot coater that is prepared with a shim that is designed in such way that it can be used as guiding device for the elastic strands. However, the device can also be a slot coater that is V-notched for each strand and with and without guiding device attached.

Such devices are delivered for example by the company Nordson Corporate, such as for example Speed-Coat™ Slot applicator.

In the present process, a compression device including a compression means with a patterned surface structure is used to provide the pre-determined surface pattern to the elastic laminate.

It has been surprisingly found that by individually coating each elastic strand, e.g. by means of slot coating, in combination with compression with a compression device having patterned surface structure, a product can be obtained which is cloth-like, soft, has a desired corrugation pattern, which is aesthetically attractive, which maintains its structure also after it has been folded, i.e. no permanent folds will be created in the product after folding, and which is flexible and breathable.
Elastic Strands Herein, the term "elastic strand" is intended to mean a strand or a thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The strands may be of the elastane type that is available under the trade name "LYCRA", but any suitable elastic strand may be used. The strands may have a linear mass density, dtex, of about 80-800 dtex.

The elastic strands are elongated during the production process from about 30 to about 300% of the initial, non-tensioned original length, 70-250%, or 100-200% of the initial, non-tensioned original length. In certain embodiments, the elastic strands are of a type that are able to tolerate an elongation of at least about 200% without breaking, so that they can be safely used in the production process without risk for breaking.

The elastic strands are arranged in parallel to each other and can be provided to the process from a multi-strand roller. The strands are spaced from each other, and with about 1-20 strands per centimetre, about 1 to 10 strands per centimetre, or about 2-6 strands per centimetre.

The spacing between the strands in the laminate may be for example of from 0.5 to 10 mm, whereby an elastic laminate with sufficient elasticity and comfort can be provided.
Nonwoven Layers The nonwoven material layers or webs may advantageously be selected from, for example, of spunbond, air laid, wet laid, carded or meltblown nonwovens. The nonwoven material may be bonded by multiple techniques, e.g. by needling, hydroentangling, or heat bonding.

The fibres constituting the nonwovens may be made of natural or synthetic materials, such as cellulosic fibres, regenerated cellulose, polyester fibres, polypropylene fibres, polyethylene fibres or the combination thereof or the like.

The nonwoven material may be a laminate or a combination of several types of nonwoven materials, such as spunbond-meltblown or spunbond-meltblown-spunbond-type. In particular embodiments, the nonwoven material is not elastic.

The basis weight for the nonwoven layer can be varied of from 5 to 80 $g/m^2$, from 10 to 40 $g/m^2$, or from 10 to 30 $g/m^2$. When the basis weight is under 40 $g/m^2$, sufficient breathability, drapeability and comfort for the product can be obtained. The basis weight of from 10 to 30 $g/m^2$ has been found to provide best comfort and flexibility while processability of the material is still good.

The various nonwoven material layers of the elastic laminate may be of the same or different materials and may have the same, similar or different basis weights. If different materials are selected, an elasticised web is attainable having different surface characteristics across the web. For example, the layers may have different friction properties or different liquid/vapour permeability properties.
Adhesive In particular embodiments, the adhesives used for coating the strands are hot-melt adhesives, which have thermoplastic properties. Any type of known hot-melt adhesive may be used and the hot-melt adhesive may be for example based on ethylene-vinyl-acetate (EVA), polyolefin, polyester and/or polyamide, polyurethane, styrene block copolymer, silicone rubber and/or natural soy protein based adhesives.

The adhesive should be non-toxic and it should be approved to be used in connection with personal hygiene products. In particular embodiments, the adhesive is a styrene block copolymer based hot-melt adhesive, such as a product similar to a product with a trademark Henkel Dispomelt 5482. Other examples of suitable hot-melt adhesives are produced by for example the company H.B. Fuller, for example products with the product name NW1002 or FC8200, and Bostic H4281.
Elastic Laminate The elastic laminate includes two nonwoven layers and a plurality of elastic strands arranged in parallel and located between the two nonwoven layers. As indicated above, the elastic strands are stretched and individually coated with an adhesive, and the nonwoven layers are attached to the elastic strands. At least one of the elastic nonwoven layers is attached to the strands at distinct adhesive bonding points in a repeating predetermined pattern in a lengthwise direction along the strands. The distinct adhesive points provided by a compression cylinder having a predetermined surface structure form a predetermined corrugation pattern for the laminate. In particular embodiments, both the first and the second nonwoven layers are attached to the strands at predetermined locations, i.e. at the predetermined adhesive bonding points.

The adhesive bonding points may have a distance between them from 0.3 to 10 mm, from 0.3 to 7 mm, or from 0.5 to 4 mm along the length of the elastic strands. These distances have been found to be short enough to provide sufficient amount of adhesive bonding points to the laminate. At the same time, the distance is long enough to provide a corrugation pattern, in which a sufficient amount of nonwoven material layer free of adhesive is on the topmost surface of the laminate. By topmost surface is meant the surface of the first nonwoven layer which is not attached to the elastic strands at the distinct adhesive bonding points after the elastic strands have been relaxed. The nonwoven material layer free of adhesive provides a smooth and soft surface for the laminate.

The length of each bonding point, i.e. the length in the lengthwise direction of the strands, may be of from 0.2 to 10 mm, 0.3 to 7 mm, or 0.5 to 3 mm. For example, the length of each bonding point may be equal to the distance between each bonding point to assure that a regular corrugation pattern is achieved. The length of from 0.2 to 10 mm provides a laminate having optimal corrugation pattern and thus optimal softness for the product.

Since only the elastic strands are adhesive coated, the nonwoven layers are substantially free of adhesive outside the areas where the layers are attached to the elastic strands. The nonwoven layers may therefore not be in direct contact with each other at the adhesive bonding points, but may instead only be joined via the elastic strand.

The adhesive from the elastic strand may be partially transferred to the first or second nonwoven material, even over substantially the whole length of the elastic strands. In the areas where the adhesive has been transferred to the nonwoven materials between the bonding points, the elastic may temporarily bond to the nonwoven materials. However, compression forces applied to the layers are much lower in the areas of the temporary bonds than in the bonding points and thus the bonding strength is much lower. These weak temporary bonds will break when the stretch of the elastic threads is released as the relaxing forces of the elastic strands will force the nonwoven materials to move away from the elastic strands to form the raised parts of the corrugations.

Process and Apparatus Used in the Process

The process for the production of the laminate will be now further described with reference to FIG. 3.

Figure 3:
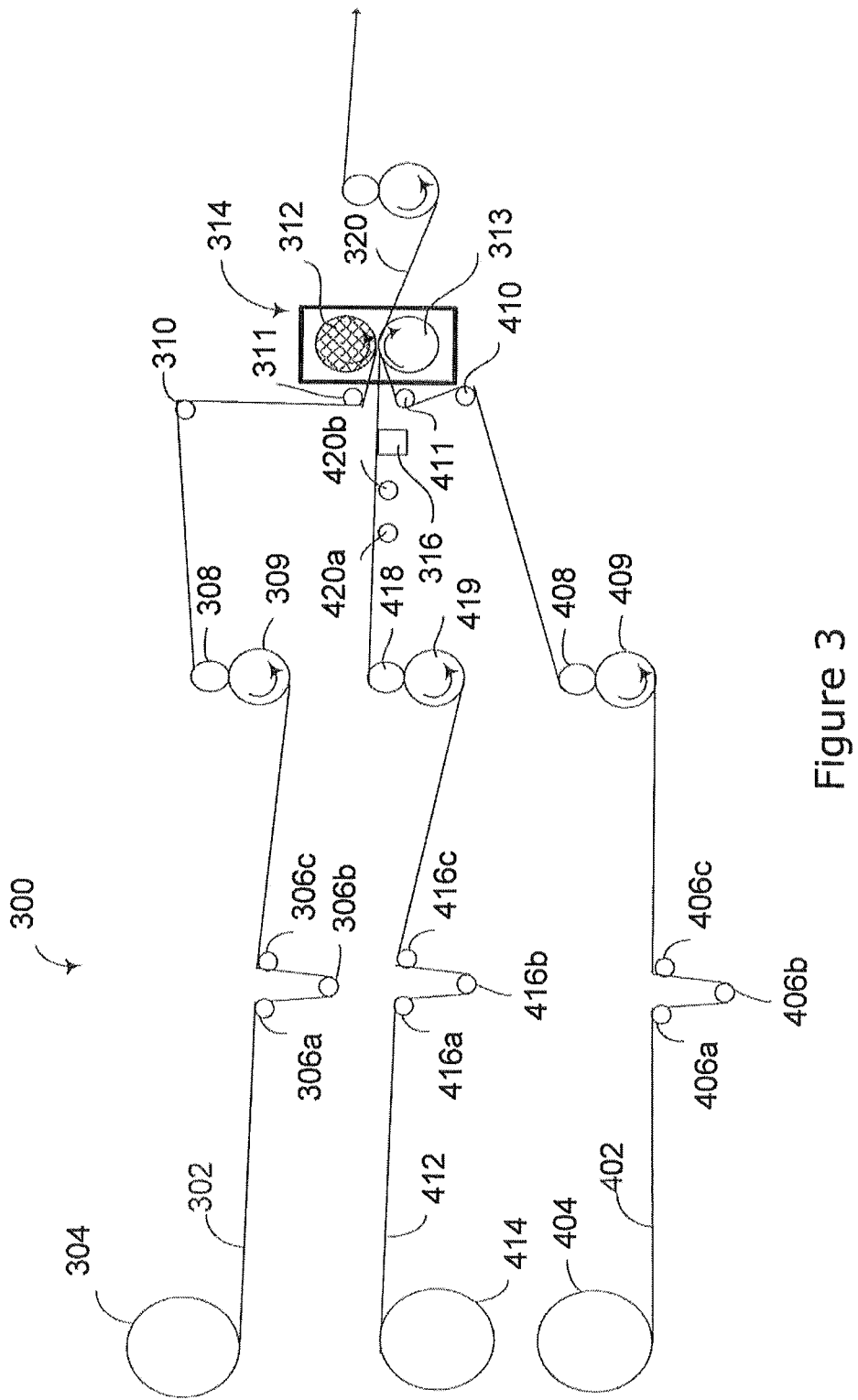
FIG. 3 is a schematic view of a process to produce an elastic laminate according to one embodiment of the present invention.

FIG. 3 shows schematically a lamination process for the production of an elastic laminate as described above. The process is depicted by the reference sign 300. In the process and in the product produced by the process, a first nonwoven web 302 forms a first nonwoven layer of the laminate and the second nonwoven web 402 forms a second nonwoven layer of the laminate.

The first nonwoven web 302 is fed from a nonwoven web roll 304 through dancer cylinders 306a, 306b and 306c to nip cylinders 308, 309. The dancer cylinders are movable in relation to each other and can in that way adjust the tension of the web 302. The first web 302 is then fed from the nip cylinders 308, 309 through guide cylinders 310, 311 to compression cylinders 312, 313, in between which the laminate is formed.

In a similar way, the second nonwoven web 402 is fed from a nonwoven web roll 404 through dancer cylinders 406a, 406b and 406c to nip cylinders 408, 409. The dancer cylinders adjust the tension of the web 402 in a similar manner as dancer cylinders 306a-306c. The second web 302 is then fed from the nip cylinders 408, 409 through guide cylinders 410 and 411 to compression cylinders 312, 313, in between which the laminate is formed.

The plurality of elastic strands 412 are fed to the process in parallel from individual rolls or a multi-strand roll 414. The strands are tensioned by means of dancer cylinders 416a, 416b, 416c to an extension of at least about 30%. The dancer cylinders 416a-416c are movable in relation to each other whereby it is possible to adjust the tension and the elongation of the strands. The strands are then fed to the nip rollers 418, 419, in which all the webs and strands are in phase. Additional tensioning or adjusting devices 420a, 420b are incorporated in the process to ensure that the tension of the strands is equal and correct for the strands. The strands are then coated with an adhesive by means of a comb-slot coating device 316, which is shown schematically, but more in detail in FIG. 6.

Figure 6:
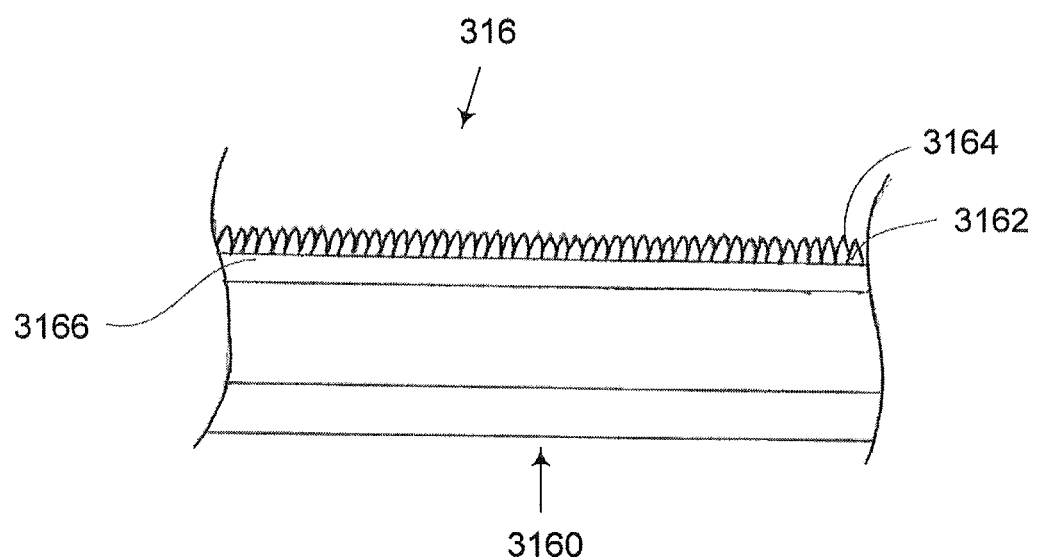
FIG. 6 shows schematically a view of a comb-slot adhesive coating device.

As can be seen in FIG. 6, the comb-slot device 316 includes a body part 3160 and a plurality of protruding pins 3162. There is a slot 3164 in between the protruding pins 3162 and each individual strand is guided through respective slot 3164. The body part 3160 includes a casing 3166 which houses the hot-melt adhesive. The adhesive is heated and pumped into the slots 3164 and thus, when the strand is guided through the slot 3164 it will be coated or impregnated with the adhesive. The comb-slot device 316 is placed in the process so that the pins 3162 are directed upwards to simplify the guidance of the strands in the comb-slot device. It is of course possible to place the device so that the pins 3162 face downwards. This would simplify the pumping of the adhesive into the slots.

Figure 7:
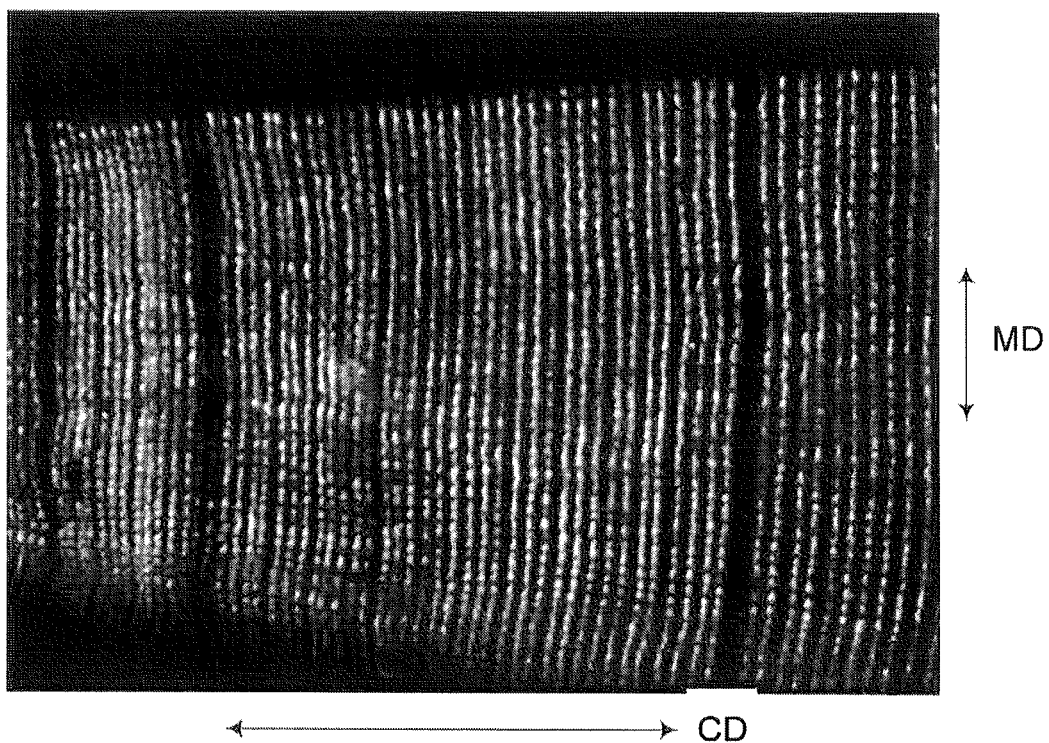
FIG. 7 is a photographic representation of the adhesive pattern according to an embodiment of the present invention.

FIG. 7 shows a photograph of slot-coated elastic strands. As can be seen, the adhesive is present only on the elastic strands whereby a regular adhesive pattern is obtained and the areas outside the elastic strands are substantially free of adhesive. A machine direction of the strands is shown with arrows and "MD" and a cross direction is shown with arrows and "CD".

Returning to FIG. 3, when the strands have been coated with the adhesive, the webs 302, 402 and the elastic strands 412 are gathered in between a first and second compression means 312 and 313 in a compression device 314 to form an elastic laminate 320. The first compression means 312 has a predetermined surface pattern, and the second compression means 313 has a substantially flat surface, i.e. it does not have a predetermined surface structure.

Figure 4:
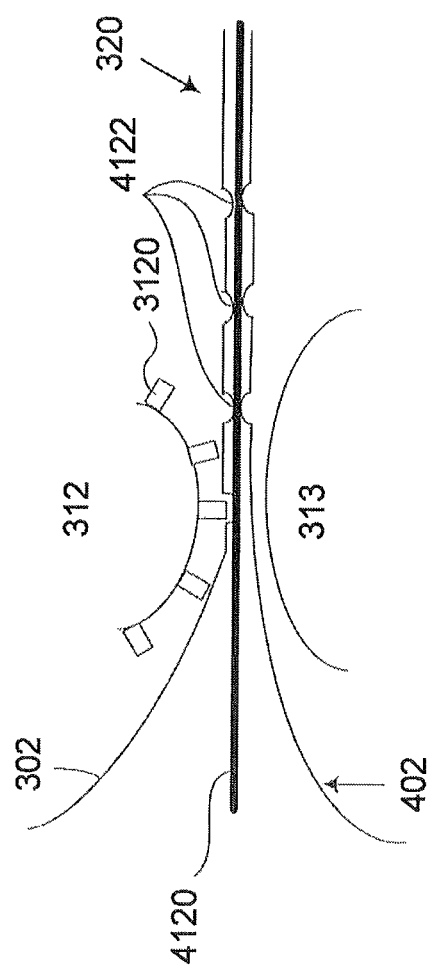
FIG. 4 is a schematic enlarged view of a nip between the first and second compression means in a compression device.

The nip between the first compression means 312 and the second compression means 313 is shown schematically, but more in detail, in FIG. 4. As can be seen, the protrusions 3120 in the first compression means 312 press the nonwoven webs 302 and 402 towards the elastic strand 4120 and the second compression means 313. The adhesive is pressure sensitive and provides a seal at predetermined bonding points 4122 to the nonwoven webs 302, 402 and the strand 4120 after compression and thereby an elastic laminate 320 is provided.

The formed elastic laminate 320 will therefore have a predetermined corrugation pattern on the side facing the first compression means 312. On the side facing the second compression means 313, adhesive may be partially transferred to the second nonwoven layer over substantially the whole length of the elastic strands. As already mentioned above, in parts of the area where the adhesive has been transferred between the bonding points there may occur weak temporary bonds that will break when the stretch of the elastic strands is released so that the elastic strands relax and contract, thereby corrugating the nonwoven webs. The first nonwoven layer 302 may have small isolated areas of adhesive outside the adhesive bonding points and the second nonwoven layer 402 is substantially free of adhesive outside the areas where it is in contact with the elastic strands.

The compression device useful in the process includes a first compression means, which can be for example a plate or a cylinder having a predetermined surface pattern, and a second compression means on the opposite side of the laminate web to be formed. By predetermined surface pattern is meant a pattern provided by e.g. protrusions or grooves on the surface of the compression means. The first nonwoven web forming the first nonwoven layer of the laminate and the second nonwoven web forming the second nonwoven layer of the laminate are pressed against the elastic strands on opposite sides of the strands in the nip between the first and second compression means. The second compression means may have the same shape as the first compression means, and can thus also be a plate or a cylinder.

The predetermined surface pattern is obtained by providing protruding elements on at least the surface of the first compression means. The surface pattern could also be provided by grooves. The first compression means is a cylinder or a drum, which rotates at the same speed as the nonwoven webs and the elastic strands, whereby it can be easily assured that the bonding points are provided on the elastic strands in a continuous manner.

The second compression means may be flat or may have a predetermined surface structure. If the second compression means has a flat surface somewhat more adhesive may be transferred to the nonwoven web than if the second compression means has a predetermined surface structure. The bonding pattern will however not change. If the second compression means has a predetermined surface structure the shape of its protrusions may correspond to the protrusions of the first compression means and the first and the second compression means are in phase with each other. This means that the protruding parts of the compression means are aligned with each other such that they meet each other on the opposing sides of the web during the production process and thereby provide a nip between the compression means so that sufficient compression is provided in the bonding points and the desired corrugation pattern can be provided to the laminate.

The predetermined pattern on the first compression means, and thus the adhesive bonding points, may have a distance of protrusions from 0.3 to 10 mm, from 0.3 to 7 mm, or from 0.5 to 4 mm. The distance of the protrusions on the first compression means defines the distance of the adhesive bonding points in the laminate. These distances have been found to be short enough to provide sufficient amount of adhesive bonding points to the laminate, while the distance is long enough to provide a corrugation pattern, in which a sufficient amount of nonwoven material layer free of adhesive is on the topmost surface, i.e. on the surface of the first nonwoven layer attached to the elastic strands at the distinct adhesive bonding points, after the elastic strands have been relaxed. The areas in the nonwoven material layer free of adhesive provide a smooth and soft surface for the laminate.

The protrusions may have a height from 0.1 mm to 5 mm, from 0.2 to 2 mm. The protrusions may be higher than 5 mm but even though the obtained compression may be better, the machine may be more vulnerable to production problems. The thicker the nonwoven layers and the elastic strands, the higher the protrusions should be.

Figure 5:
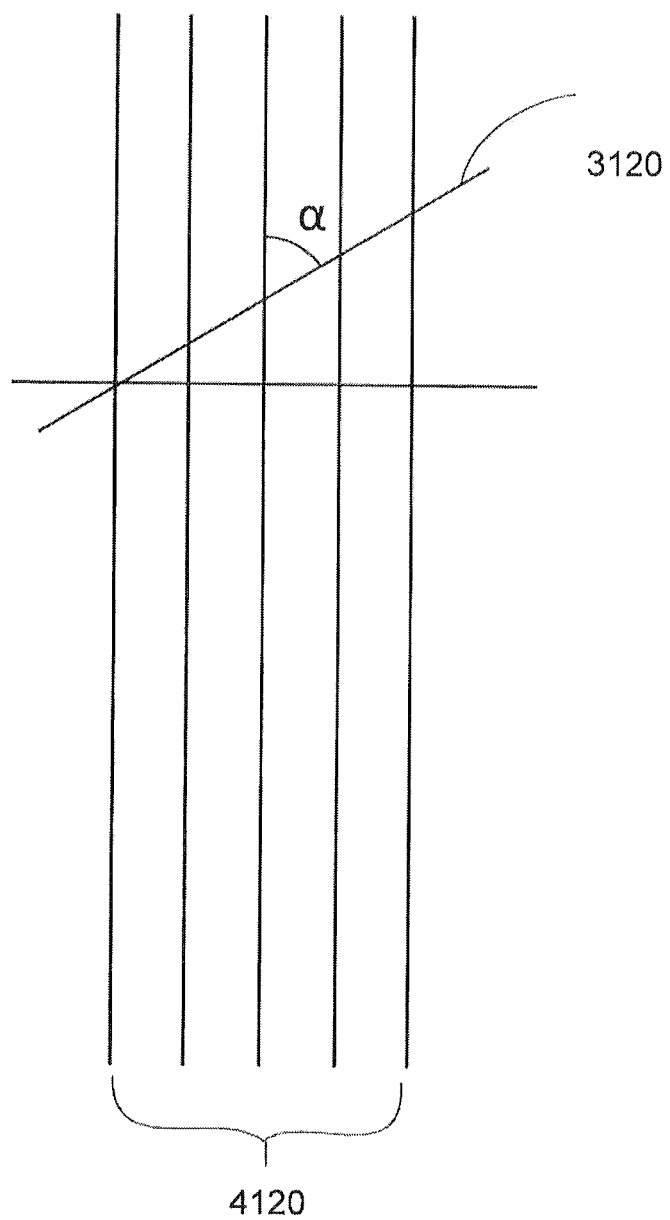
FIG. 5 shows schematically the angle α at which the predetermined corrugation pattern crosses the direction of the elastic strands.

The angle α of the predetermined straight line-shaped protrusion 3120 in relation to the longitudinal direction of the strands 4120 is shown schematically in FIG. 5. As already mentioned above, the inclination of the protrusions 3120 and thus the formed corrugation pattern decreases the line pressure variations and thus decreases for example vibrations during the process. The predetermined corrugation pattern crosses the direction of the elastic strands at an angle α of at least 45°, at least 60°, at least 80°, or at least 85° to the direction of the elastic strands. The angle could be in a corresponding way over 90°, but less than 95°. Alternatively, the angle α is equal to or less than 135°.

Figure 8:
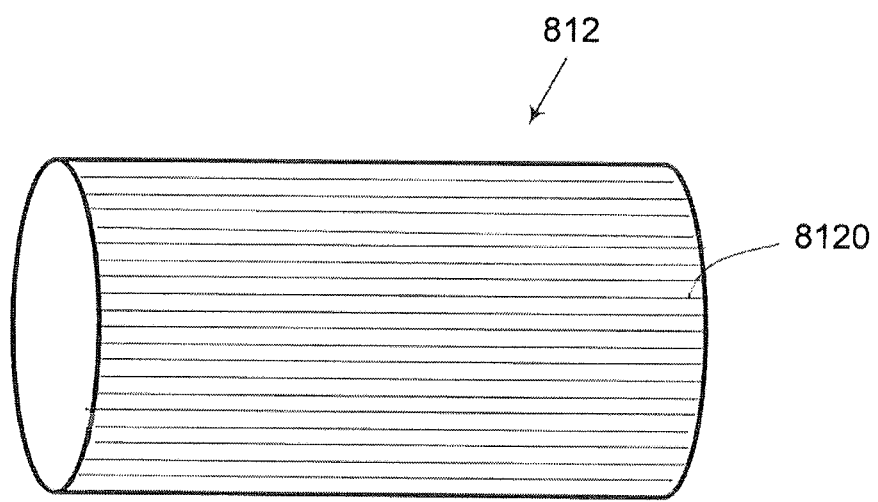
FIG. 8 is a schematic perspective view of a first compression means having straight line-shaped protrusions.

FIG. 8 shows schematically an example of a first compression means in a compression device. The means is a cylinder 812 including a plurality of straight-line shaped protrusions 8120 and the cylinder thus has a protruding straight-line shaped surface structure.

Figure 9:
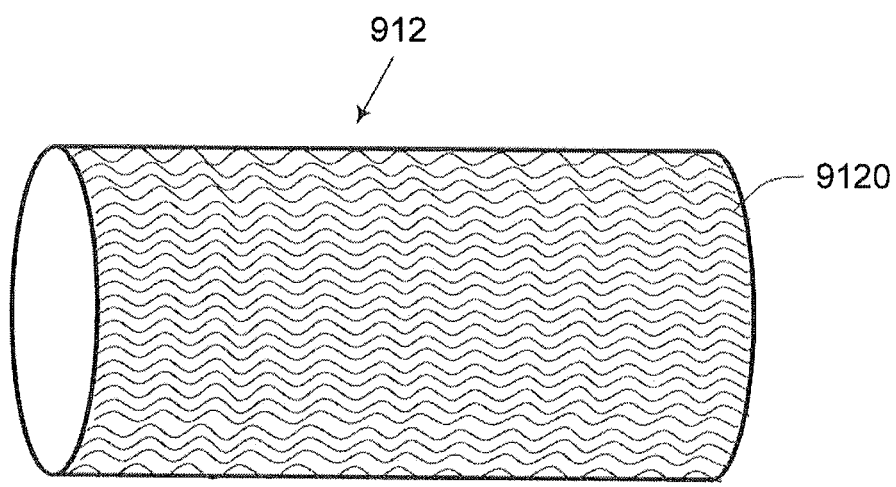
FIG. 9 is a schematic perspective view of a first compression means having wave-shaped protrusions.

FIG. 9 shows schematically another example of a first compression means in a compression device. The means is a cylinder 912 including a plurality of wave-shaped protrusions 9120 and the cylinder thus has a protruding wave-shaped surface structure.

Figure 10:
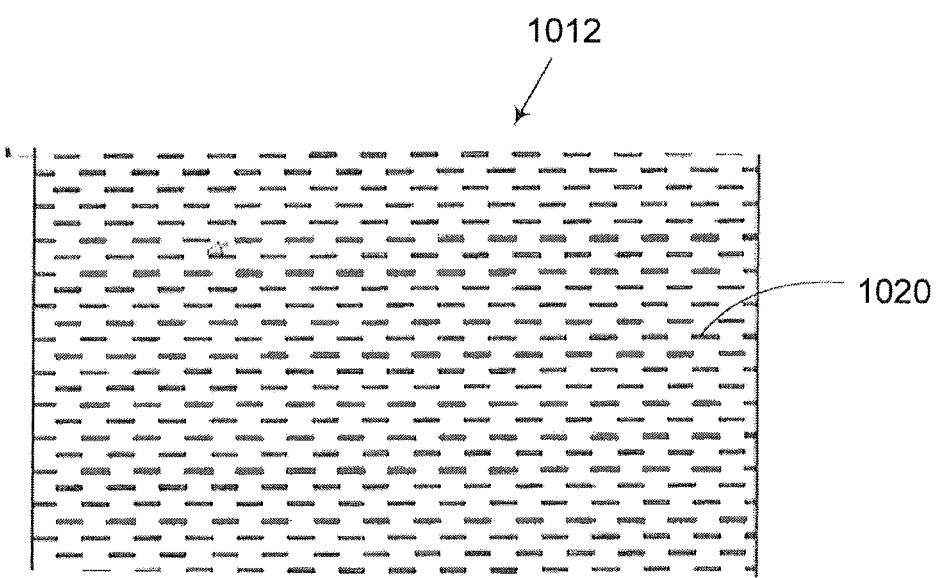
FIG. 10 is a schematic perspective view of a first compression means having short straight line-shaped protrusions.

FIG. 10 shows schematically a further example of a first compression means in a compression device. The means is a plate 1012 including a plurality of short straight-line shaped protrusions 1020 and the plate thus has a protruding straight-line shaped surface structure.

Figure 11:
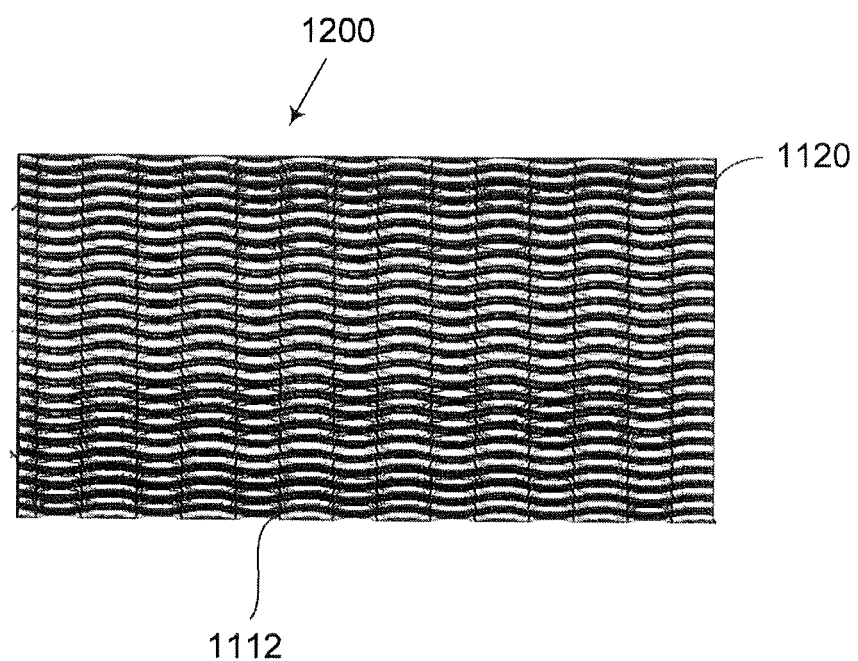
FIG. 11 is a schematic illustration of a laminate having a wave-shaped corrugation pattern according to one embodiment of the present invention.

In FIG. 11, an example of an obtained corrugated laminate 1200 with a wave-shaped corrugation pattern is shown schematically. The laminate includes a plurality of elastic strands 1112. As can be seen, the obtained corrugation pattern 1120 is wave-like and is obtained by means of a compression device including a wave-like surface structure, e.g. as shown in FIG. 9.

Absorbent Products

The elastic laminate may be used in numerous applications, for example in absorbent products. Such products may include diapers, incontinence protection garments, sanitary napkins, panty shields and the like.

In absorbent products, such as diapers or adult incontinence products, it is desirable to provide selected regions with greater elasticity than other regions, for example in the waist region, the hip region and leg openings. This provides a product with optimal fit and comfort. The hip region is defined as the region below the waist region and above the crotch region. It includes the hips, the abdominal region and the lower part of the back and the upper parts of the buttocks that are at the same height as the hips.

An absorbent product generally includes a chassis and an absorbent structure within the chassis. The chassis includes a front panel and a rear panel. The front panel is intended to overlie the abdominal region of the wearer and the rear panel is intended to overlie the lower back and buttocks region. The absorbent product also has a crotch region extending between the front panel and the rear panel. The crotch region may be made of the absorbent structure and sometimes also the chassis of the product. Typically, the absorbent structure further includes an absorbent core located primarily in the crotch region but can also extend into the front panel and the back panel of the chassis, with the absorbent core being sandwiched between a liquid pervious top sheet and a generally liquid impervious backsheet. The outer cover of the chassis may also be the liquid impervious backsheet of the absorbent structure.

The absorbent core may include any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like.

The liquid permeable topsheet can include a nonwoven material, e.g. spunbonded, meltblown, carded, hydroentangled, wetlaid, etc. which can be composed of natural fibers, such as woodpulp or cotton fibres, synthetic fibres, such as polyester, polyethylene, polypropylene, viscose, etc. or from a mixture thereof. The topsheet material may further be composed of tow fibres, porous foams, apertured plastic films etc. The materials suited as topsheet materials should be soft and non-irritating to the skin and be readily penetrated by body fluid, e g urine or menstrual fluid, and display low rewetting properties.

The liquid impermeable backsheet may include a thin plastic film, e.g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent core, while still preventing liquids from passing through the backsheet material.

The top sheet and backsheet may be connected to each other for example by adhesive bonding, gluing or welding by heat or ultrasonic. The topsheet and/or the backsheet may further be attached to the absorbent core by any method known in the art, such as adhesive, heat-bonding etc.

An absorbent product in the form of for example a diaper may also include fastening means for securing the front and rear end regions to each other to thereby secure the diaper around the waist of a wearer. This type of a diaper is a conventional open diaper.

The disposable absorbent product may also be in the form of a belted absorbent product. These products are generally worn by adults and may be adapted for both incontinence and general use. A belted absorbent product is provided with two belt halves extending from the lateral sides of the rear end region. The belt halves are intended to be placed around the waist of a wearer and fastened using any suitable fastener to retain the belted absorbent product around the waist of a wearer.

The disposable absorbent product may also be in the form of a pant type diaper. In contrast to a conventional open diaper, the front and rear end regions of a pant-type diaper are initially secured to each other by means of side seams to thereby provide a garment which can be drawn up on a wearer in the same manner as a normal undergarment. The side seams may be made to be rupturable.

The absorbent product, i.e. for example a conventional diaper, belted absorbent product or pant type diaper or any other absorbent product, includes at least one region including the elastic laminate and as described earlier. The region can at least partially includes a waist region and/or the hip region of the absorbent product to provide comfort and fit around the waist. The region may also be a leg structure in the crotch region, whereby the elastic laminate can provide a sealing effect around the upper leg region of a wearer of the absorbent product to thereby reduce the risk of leakage of bodily discharges from the absorbent product. The elastic laminate may also constitute at least a part of a standing gather structure in the crotch region of the absorbent product or it can be a part of a crotch elastic structure in the crotch region. The crotch elastic structure serves i.a. to encourage the absorbent product to adopt a bowl shape in the crotch region when the product is worn to thereby assist in retaining discharged bodily wastes. The corrugated laminate is especially suited to be used as waist elastic and/or the hip elastics in pant diapers.

The positive effects obtained by the elastic laminate have been further shown in the following examples.

Examples

Two different elastic laminates, Laminate A and Laminate B, were prepared. Both laminates have similar elastic properties. Elastic laminate A is a laminate according to one embodiment of the present invention and has the following features:

Laminate A

According to One Embodiment of the Invention

First nonwoven layer: spunbonded nonwoven
Basis weight: 19 $g/m^2$
Second nonwoven layer: spunbonded nonwoven
Basis weight: 19 $g/m^2$
Elastic strands: spandex 240 dtex
Separation: 2 mm
Adhesive: Hotmelt, V-slot on threads; 0.01 g/m on thread The first nonwoven layer is the layer facing the first compression means with a predetermined surface pattern. The second compression means has a flat surface structure.

Laminate B

Comparative Example

First nonwoven layer: spunbonded nonwoven
Basis weight: 19 $g/m^2$
Second nonwoven layer: spunbonded nonwoven
Basis weight: 19 $g/m^2$
Elastic strands: spandex 240 dtex
Separation: 2 mm
Adhesive: Hotmelt, spray glued, 4.7 $g/m^2$, The laminate is bonded by the use of two flat compression means.

Analysis 1—Sensory Panel

The smoothness of the two laminates was evaluated in a sensory test panel. In sensory panels test members are asked to evaluate a property that is opposite of the one that is desired. In this case, smoothness is the required property and thus the panel members are asked to evaluate which of the samples is the roughest.

The sensorial test was performed by arranging a blind test with 20 panel members. The two different samples, Laminate A and Laminate B, were placed randomly on a table. In connection with Laminate A, the side with the first nonwoven layers was facing upwards towards the test persons in the test.

In connection with Laminate B, the side on which the hot-melt adhesive was sprayed was facing upwards towards the test persons.

The test persons were not allowed to see the samples or lift them from the table. They were asked to slide the finger tips over the material surfaces from left to right and tell which one was the roughest.

The results gave a significant difference in favour of the laminate with glue applied on individual strands, Laminate A. 17 out of 20 members considered Laminate A, that is the Laminate, to be the least rough, i.e. the smoothest.

Analysis 2—Kawabata

Surface properties of the two laminates were measured using Kawabata Evaluation System, KES-FB, a Japanese quality judgment system used for textile materials and is disclosed in: "*The Standardization and Analysis of Hand Evaluation (2nd Edition), Sueo Kawabata, July* 1980, *The Hand Evaluation and Standardization Committee, The Textile Machinery Society of Japan.*"

Special recommendations for nonwoven materials are set up in: "*A Proposal of the Standardized Measuring Conditions for Mechanical Property of Apparel Fabric, by Kawabata S och Niwa M*" These recommendations have been followed in the tests below with the following exceptions: The material width was 140 mm instead of 200 mm due to practical reasons and the weight of the bar which loads the samples was 120 g.

The Kawabata test is divided into four blocks: KES-FB-1 for tensile- and shear measurements, KES-FB-2 for pure bending measurements, KES-FB-3 for compression measurements and KES-FB-4 for surface measurements.

Examples of output data obtained from Kawabata tests are:

Extensibility (%)
Bending rigidity (gf cm2/cm)●Shear stiffness (gf/cm degree)
Compressibility (%)
Surface roughness (μm)
Friction (-)

The unit gf used in the Kawabata system is the force which gravity exerts on one gram, i.e. about 9.81 mN. In our tests, only the Surface roughness and Friction (KES-FB-4) module have been used. A low Surface roughness and Friction is known to cause less chafe for a wearer of hygiene articles and to correlate with perceived smoothness in sensorial tests.

Friction

Figure 12A:
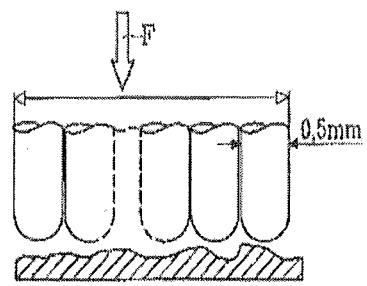
FIGS. 12 *a* and *b* illustrate the method for measuring Friction according to Kawabata.
Figure 12B:
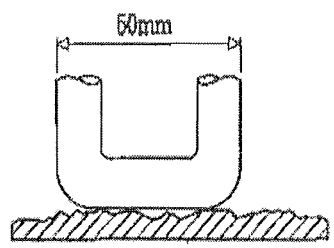

The Friction according to Kawabata is measured by drawing a "sledge" according to FIG. 12 *a* and *b*, 20 mm back and forth along the sample surface at which the force is measured. The speed in this measurement is 1 mm/s and the normal force F is kept constant=50 gf.

Surface Roughness

Figure 13A:
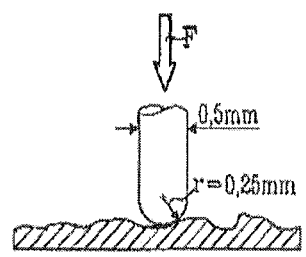
FIGS. 13 *a* and *b* illustrate the method for measuring Surface roughness according to Kawabata.
Figure 13B:
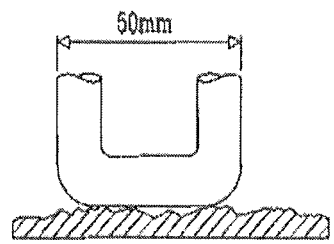

The bulb for the Surface roughness measurements consists of a smooth metal thread having a shape according to FIG. 13 *a* and *b*. It is loaded with a constant force of 10 gf and moves with a speed of 1 mm/s in 20 mm back and forth once over the sample surface. The Surface roughness is defined as the mean deviation from the thickness of the sample measured in the unit μm.

Samples having a width of 140 mm were prepared and analysed in the machine direction (MD) of the surface analysis module in the Kawabata equipment. The samples were loaded with the clamp and 120 g bar and measured in the forward and backward directions in MD. Average values of surface roughness, friction and friction variation are presented in the table below:

| Property | Laminate A | Laminate B |
|---|---|---|
| Friction | 6.05 | 6.41 |
| Friction variation | 1.63 | 2.29 |
| Surface Roughness | 8.16 | 10.53 |

Laminate B, the spray glued sample, has larger surface roughness than Laminate A. Also, friction and friction variation values are slightly higher.

Analysis 3—TSA

The exemplifying sample laminates A and B above have been analysed with TSA—Tissue Softness Analyzer, a method that uses acoustic waves and has demonstrated to correlate well with hand panel tests for thin materials like tissue or nonwoven, and has been proposed to become a new ISO standard.

Technical Basics of TSA

The hand feel of a fibrous material is affected by components at various levels; from the polymers at a molecular level to the fibrous network at a macro level. Stiffness of single fibres, internal structure, fibre-to-fibre bond strength, softener chemicals etc. all affect the hand feel, but so do also the properties of the web material such as creping, embossing, thickness etc.

The TSA analysis can because of its principle measure effects of material differences at various levels and algorithms for different types of materials such as toilet paper or facial tissue have been developed.

Measuring Principle

The sample will be fixed in a measuring cell like a drumhead. Below is placed a vibration sensor, above is placed a vertical movable measuring head with a rotating blade that will be pushed onto the sample with a defined load. In step 1 of the measurement, a rotation with defined speed will be executed. The motion of the blades over the sample generates different types of vibrations/noise, which will be detected with a vibration sensor. In step 2 of the measurement, the sample will be deformed perpendicular to the surface to measure elastic, visco-elastic and plastic properties.

Evaluation

The resulting vibrations/noise spectrum from step 1 of the measurement is an overlapping of two single spectra; (a) Vertical vibration of the sample like a membrane and (b) Excitation of horizontal vibrations of the blades itself caused by momentary blocking and swinging back of the blades by the fibres, when moving over the surface.

Figure 14:
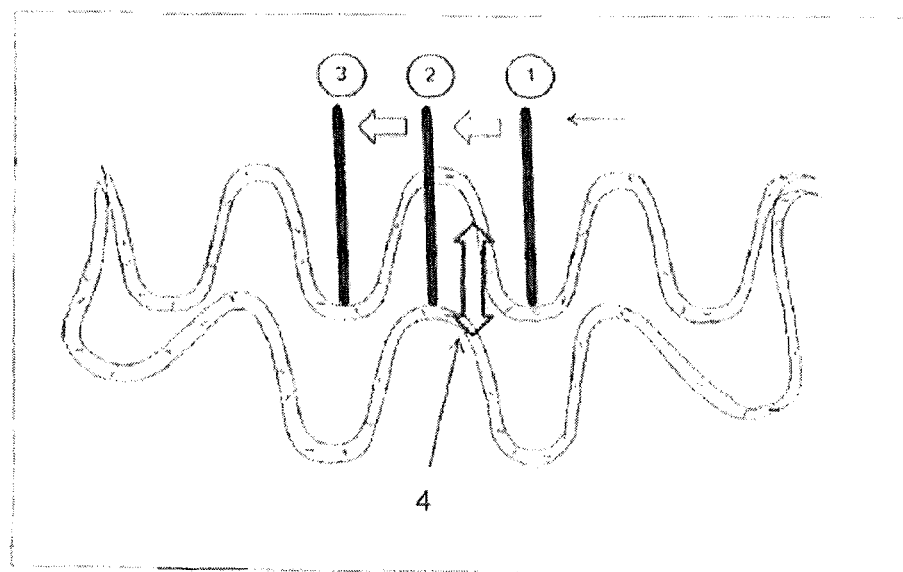
FIG. 14 illustrates vertical vibration of the sample in TSA analysis.

(a) FIG. 14 illustrates vertical vibration of the sample (arrow with reference sign 4) like a membrane, caused by the motion of the blades 1, 2 and 3 (fixed vertical position) over the sample surface with creping/embossing, similar to the needle of a music recorder movement over the record.

The vibration frequency is dependent on the structure dimensions (creping/embossing) and the rotation speed of the blade. The amplitude of the vibrations is dependent on the height of the structures.

The first peak of the spectrum represents the smoothness/roughness and is called "TS750 smoothness/roughness peak". It correlates with the perceived smoothness/roughness: the softer the material, the lower is the impact of the roughness to the hand feeling.

Figure 15:
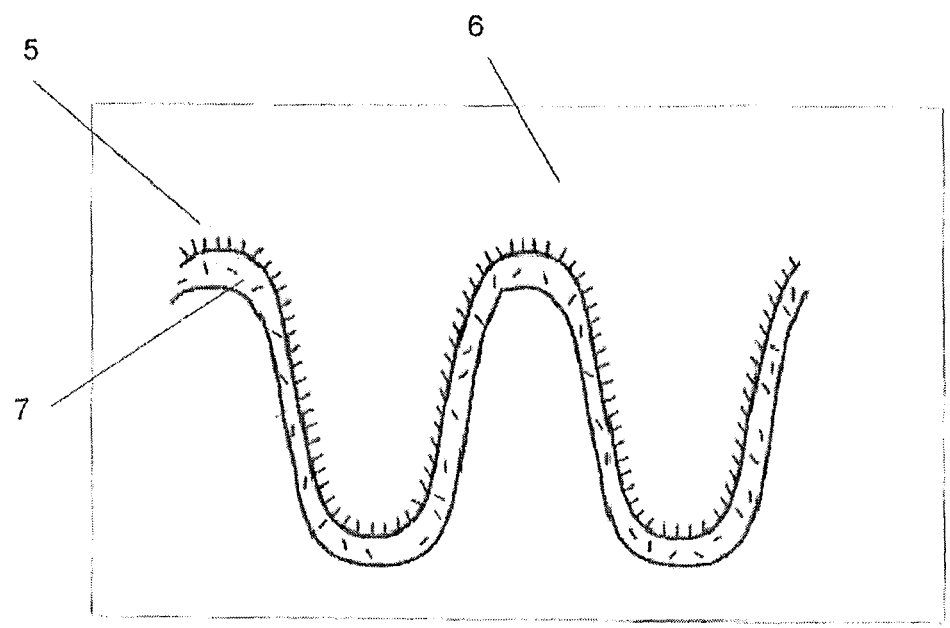
FIG. 15 illustrates the image sections for different resonance peaks in TSA analysis.

(b) Excitation of horizontal vibrations of the blades itself (in resonance frequency at approx. 6.500 Hz), caused by momentary blocking and swinging back of the blades by the fibres, when moving over the surface: the respective part of the spectrum is called "TS7 softness peak" (at 7000 Hz)

whereas the frequency is constant (dependent on the material and geometry), but the deflection is dependent on the softness/hardness of the fibers (stiffness of the individual fibres) and structure of the material (bulk, binding of the fibres). The height of this peak TS7 correlates with the real material softness. FIG. 15 illustrates the image section for TS7-peak with reference sign 5, and image section for TS750-peak with reference sign 6 for a sample 7.

Figure 16:
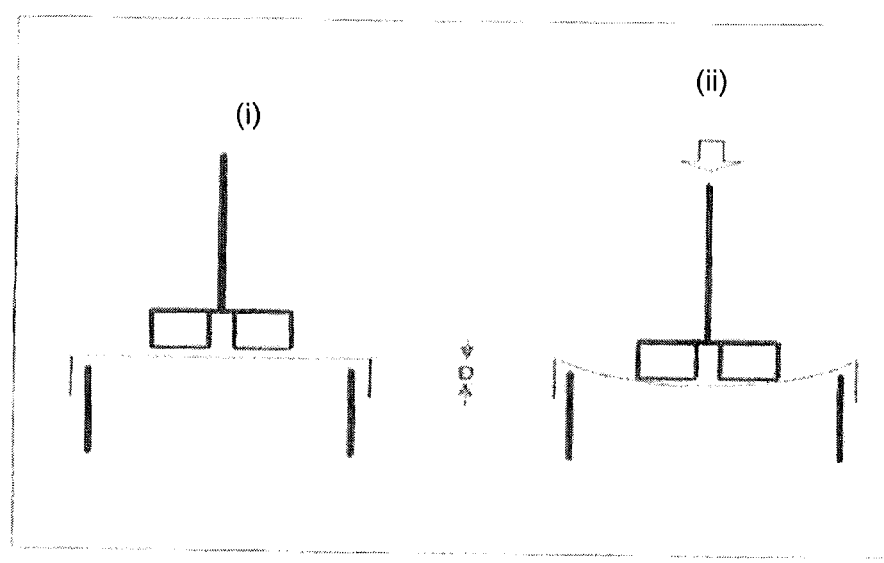
FIG. 16 illustrates the application of force in TSA analysis.

In step 2 of the measurement, the rotor applies a defined load in three cycles in vertical direction onto the sample. FIG. 16 illustrates the application of force. In step (i) F=100 mN and in step (ii) F is constant and 600 mN. The measured deformation D correlates with the stiffness of the material.

The three parameters TS7 softness, TS750 smoothness and D stiffness will be combined together with the calliper (thickness), grammage and number of plies with different algorithms to a hand feel number HF=f(TS7, TS750, D, Caliper, Grammage, no. of plies). The mathematical equations can be created in a way that the results correlate with a certain panel. Standard algorithms for each material (base tissue, toilet paper, facials) are available by the instrument producer.

Laminates A and B were analysed according to the descriptions above, using a TSA equipment provided by the company EMTEC. The tests were performed in accordance with the instructions for the EMTEC equipment.

A table with the key results from the TSA measurement is seen below.

|  | Laminate A | Laminate B |
| --- | --- | --- |
| TS7 (dB V^2 rms) | 7.857 | 8.102 |
| TS750 (dB V^2 rms) | 27.938 | 51.605 |
| D (mm/N) | 4.60 | 3.77 |
| HF | 74.4 | 69.9 |

As can be seen from the results, the deformation D is higher for Laminate A. Laminate B has a higher resistance to the applied force and deforms to a less extent under the load.

The TS750 value is significantly higher for Laminate B which could be interpreted as that this material has a higher perceived stiffness than Laminate A.

The TS7 values are similar for Laminate A and B but slightly lower for Laminate A. Both laminates include same nonwoven layer materials.

An algorithm developed for facial tissue materials (Facial II) was used to correlate TSA data with hand feel values and sample A is approximately 5 units softer than B on a 100 graded scale.

The results show that the Laminate A is softer and has a smoother surface structure than the prior art Laminate B.

The invention has been described above by way of example only and it is to be understood that the invention may be varied in many ways within the scope of the appended claims.

The invention claimed is:

1. An elastic laminate comprising:
   a first nonwoven layer;
   a second nonwoven layer; and
   a plurality of elastic strands arranged in parallel with one another between said first and second nonwoven layers, wherein each elastic strand is individually coated with a hot-melt adhesive along a length of the elastic strand, wherein:
   the first and second nonwoven layers are attached to the plurality of elastic strands only at distinct bonding points in a repeating predetermined pattern in a lengthwise direction along the elastic strands in a stretched state such that some portions of the elastic strands that are coated with the adhesive are bonded to the first and second nonwoven layers at the distinct bonding points, and that other portions of the elastic strands that are between the distinct bonding points and that are coated with the adhesive are not bonded to the first and second nonwoven layers;
   the elastic laminate is compressed at the distinct bonding points to a thickness that is less than a thickness of the elastic laminate between the bonding points;
   when the elastic strands are in a relaxed state the first and second nonwoven layers are corrugated, and
   the first and second nonwoven layers are substantially free of adhesive, except in the distinct bonding points.

2. The elastic laminate according to claim 1, wherein, in the stretched state during production, the elastic strands are stretched from 30% to 200% of an initial, non-tensioned original length.

3. The elastic laminate according to claim 1, wherein the distinct bonding points are formed by compression of the elastic laminate at the distinct bonding points.

4. The elastic laminate according to claim 1, wherein the laminate is elastic in the longitudinal direction of the strands and the repeating predetermined pattern of the distinct bonding points forms lines crossing the direction of the elastic strands at angle α of at least 45° to the direction of the elastic strands.

5. The elastic laminate according to claim 1, wherein the predetermined pattern of the distinct bonding points comprises straight lines or wave-shaped lines in a direction perpendicular to the direction of the elastic strands.

6. The elastic laminate according to claim 1, wherein at least one of the first or the second nonwoven layer comprises a meltblown or spunbond or spunlaced spunbond nonwoven layer.

7. A process for the manufacture of an elastic laminate in a lamination process comprising:
   feeding a first nonwoven web to the lamination process;
   feeding a second nonwoven web to the lamination process;
   feeding a plurality of elastic strands in parallel to the lamination process; stretching the elastic strands;
   individually coating by slot coating an adhesive along a length of each of the elastic strands;
   compressing the first and second nonwoven webs and the stretched, adhesive coated elastic strands together by at least one compression device comprising a first compressor and a second compressor to form a laminate, wherein at least the first compressor has a predetermined surface pattern to form distinct adhesive bonding points in a repeating predetermined pattern in a lengthwise direction along the elastic strands such that some portions of the elastic strands that are coated with the adhesive are bonded to the first and second nonwoven layers at the distinct adhesive bonding points, and that other portions of the elastic strands that are between the distinct adhesive bonding points and that are coated with the adhesive are not bonded to the first and second nonwoven layers, and such; and
   relaxing the elastic strands in the formed laminate to form a corrugated elastic laminate with a predetermined corrugation pattern.

8. The process according to claim 7, wherein the stretching step includes stretching the elastic strands from 30% to 200% of an initial, non-tensioned original length.

9. The process according to claim 7, wherein the plurality of elastic strands are coated by slot-coating.

10. The process according to claim 7, wherein at least the first compressor has a protruding straight-line shaped surface structure.

11. The process according to claim 7, wherein at least the first compressor has a protruding wave-line shaped surface structure.

12. The process according to claim 7, wherein the at least first compressor includes a compression cylinder.

13. The process according to claim 7, wherein the second compressor has the predetermined pattern and is in phase with the predetermined pattern on the first compressor.

14. An absorbent product comprising the elastic laminate according to claim 1.

15. The absorbent product according to claim 14, wherein the elastic laminate is comprised in at least the waist region or the hip region of the absorbent product.

16. The elastic laminate according to claim 1, wherein each elastic strand is individually coated with the hot-melt adhesive along substantially the whole length of the elastic strand.

17. The process according to claim 7, wherein each elastic strand is individually coated with the hot-melt adhesive along substantially the whole length of the elastic strand.

18. The process according to claim 7, wherein the first and second nonwoven webs and the stretched, adhesive coated elastic strands are compressed together such that the elastic laminate is compressed at the distinct bonding points to a thickness that is less than a thickness of the elastic laminate between the bonding points.

* * * * *